US00PP35295P2

(12) United States Plant Patent
van Haaster et al.

(10) Patent No.: US PP35,295 P2
(45) Date of Patent: Aug. 1, 2023

(54) ***DAHLIA* PLANT NAMED 'DODAHYPROSWI'**

(50) Latin Name: *Dahlia variabilis*
Varietal Denomination: Dodahyproswi

(71) Applicant: DUMMEN GROUP B.V., De Lier (NL)

(72) Inventors: Ans van Haaster, Hillegom (NL); Arjan Koot, Oeffelt (NL)

(73) Assignee: Dummen Group B.V., De Lier (NL)

( * ) Notice: Subject to any disclaimer, the term of this patent is extended or adjusted under 35 U.S.C. 154(b) by 0 days.

(21) Appl. No.: 18/081,158

(22) Filed: Dec. 14, 2022

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
CPC ..... A01H 5/02; A01H 5/00; A01H 6/14
See application file for complete search history.

(56) References Cited

PUBLICATIONS

Longfield Gardens *Dahlia* Arbatax, retrieved on Feb. 22, 2023 at https://www.longfield-gardens.com/plantname/dahlia-decorative-arbatax, 3 pp. (Year: 2023).*
Trademark Electronic Search System (TESS), retrieved on Feb. 22, 2023 at https://tmsearch.uspto.gov/bin/showfield?f=doc&state=4806:gykgeh.2.2, 2 pp. (Year: 2023).*

* cited by examiner

*Primary Examiner* — June Hwu
(74) *Attorney, Agent, or Firm* — C. Anne Whealy

(57) ABSTRACT

A new and distinct cultivar of *Dahlia* plant named 'Dodahyproswi', characterized by its broadly upright and uniformly mounding plant habit; moderately vigorous to vigorous growth habit and moderate growth rate; strong branching habit; dark green-colored leaves; freely flowering habit; large double-type inflorescences with reddish purple and white bi-colored ray florets; good postproduction longevity; and good garden performance.

1 Drawing Sheet

Botanical designation: *Dahlia variabilis*.
Cultivar denomination: 'DODAHYPROSWI'.

BACKGROUND OF THE INVENTION

The present invention relates to a new and distinct cultivar of *Dahlia* plant, botanically known as *Dahlia variabilis* and hereinafter referred to by the name 'Dodahyproswi'.

The new *Dahlia* plant is a product of a planned breeding program conducted by the Inventors in Hillegom and De Lier, The Netherlands. The objective of the breeding program is to create new container *Dahlia* plants that have a freely branching and flowering habit, dark-colored leaves, large attractive inflorescences and good postproduction longevity.

The new *Dahlia* plant originated from a cross-pollination during the autumn of 2017 in Hillegom, The Netherlands of two unidentified proprietary selections of *Dahlia variabilis*, not patented. The new *Dahlia* plant was discovered and selected by the Inventors as a single flowering plant from within the progeny of the stated cross-pollination in a controlled greenhouse environment in Hillegom, The Netherlands during the summer of 2018.

Asexual reproduction of the new *Dahlia* plant by vegetative terminal cuttings in a controlled greenhouse environment in De Lier, The Netherlands since the autumn of 2018 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dodahyproswi'. These characteristics in combination distinguish 'Dodahyproswi' as a new and distinct *Dahlia* plant:

1. Broadly upright and uniformly mounding plant habit.
2. Moderately vigorous to vigorous growth habit and moderate growth rate.
3. Strong branching habit.
4. Dark green-colored leaves.
5. Freely flowering habit.
6. Large double-type inflorescences with reddish purple and white bi-colored ray florets.
7. Good postproduction longevity.
8. Good garden performance.

Compared to plants of the parent selections, plants of the new *Dahlia* differ primarily in growth habit as plants of the new *Dahlia* are more uniformly branching and mounding than plants of the parent selections.

Plants of the new *Dahlia* can be compared to plants of *Dahlia variabilis* HYPNOTICA 'Limoncello', not patented. In side-by-side comparisons, plants of the new *Dahlia* differ primarily from plants of HYPNOTICA 'Limoncello' in the following characteristics:

1. Plants of the new *Dahlia* are larger and stronger than plants of HYPNOTICA 'Limoncello'.

2. Plants of the new *Dahlia* have larger leaves and leaflets than plants of HYPNOTICA 'Limoncello'.
3. Plants of the new *Dahlia* have larger and taller inflorescences than plants of HYPNOTICA 'Limoncello'.
4. Plants of the new *Dahlia* have more ray florets per inflorescence than plants of HYPNOTICA 'Limoncello'.
5. Ray florets of plants of the new *Dahlia* are reddish purple and white bi-colored whereas ray florets of plants of HYPNOTICA 'Limoncello' are yellow and white bi-colored.

BRIEF DESCRIPTION OF THE PHOTOGRAPH

The accompanying photograph illustrates the overall appearance of the new *Dahlia* plant showing the colors as true as it is reasonably possible to obtain in colored reproductions of this type. Colors in the photograph may differ slightly from the color values cited in the detailed botanical description which accurately describe the colors of the new *Dahlia* plant. The photograph is a side perspective view of a typical flowering plant of 'Dodahyproswi' grown in a container.

DETAILED BOTANICAL DESCRIPTION

The aforementioned photograph and the following observations and measurements describe plants grown during the summer in 15-cm containers in a glass-covered greenhouse in De Lier, The Netherlands and under environmental conditions and cultural practices which approximate those generally used in commercial potted *Dahlia* production. During the production of the plants, day temperatures ranged from 18° C. to 30° C., night temperatures ranged from 16° C. to 22° C. and light levels were at least 135 watt/$m^2$. Plants were pinched one time about four weeks after sticking unrooted cuttings. Plants were twelve weeks old when the photograph was taken and eleven weeks old when the description was taken. In the following description, color references are made to The Royal Horticultural Society Colour Chart, 2007 Edition, except where general terms of ordinary dictionary significance are used.

Botanical classification: *Dahlia variabilis* 'Dodahyproswi'.

Parentage:

*Female, or seed, parent*.—Unidentified proprietary selection of *Dahlia variabilis*, not patented.

*Male, or pollen, parent*.—Unidentified proprietary selection of *Dahlia variabilis*, not patented.

Propagation:

*Type*.—By vegetative terminal cuttings.

*Time to initiate roots, summer*.—About twelve days at temperatures about 22° C. to 30° C.

*Time to initiate roots, winter*.—About two weeks at temperatures about 20° C. to 22° C.

*Time to produce a rooted plant, summer*.—About three weeks at temperatures about 22° C. to 30° C.

*Time to produce a rooted plant, winter*.—About 3.5 weeks at temperatures about 20° C. to 22° C.

*Root description*.—Medium in thickness, fibrous; typically whitish grey in color, actual color of the roots is dependent on substrate composition, water quality, fertilizers, substrate temperature and age of roots; tuber development has not been observed on plants of the new *Dahlia*.

*Rooting habit*.—Moderately freely branching; medium density.

Plant description:

*Plant and growth habit*.—Broadly upright and uniformly mounding plant form; broad inverted triangle; moderately freely basal branching habit with about four primary lateral branches developing per plant, each primary lateral branch with about two to four secondary branches; pinching enhances lateral branch development; inflorescences held above the foliar plane on strong peduncles; bushy and dense habit; moderately vigorous to vigorous growth habit and moderate growth rate.

*Plant height, soil level to top of foliar plane*.—About 28 cm.

*Plant height, soil level to top of floral plane*.—About 30 cm.

*Plant diameter or spread*.—About 47 cm.

*Lateral branches*.—Length: About 22 cm. Diameter: About 1 cm. Internode length: About 5.5 cm. Aspect: Mostly upright to slightly outwardly spreading. Strength: Moderately strong. Texture and luster: Smooth, glabrous; semi-glossy. Color: Close to 146B; internodes, close to 145A; with development, color becoming closer to 144A.

Leaf description:

*Arrangement*.—Opposite; leaves may be single or compound with typically three leaflets.

*Leaf length*.—About 21 cm.

*Leaf width*.—About 15 cm.

*Leaflet length*.—About 12.5 cm.

*Leaflet width*.—About 5.8 cm.

*Leaf and leaflet shape*.—Ovate.

*Leaf and leaflet apex*.—Acute.

*Leaf and leaflet base*.—Attenuate.

*Leaf and leaflet margin*.—Dentate; indentations medium in depth and divergent.

*Leaf and leaflet venation pattern*.—Pinnate.

*Leaf and leaflet texture and luster, upper surface*.—Smooth, glabrous; semi-glossy.

*Leaf and leaflet texture and luster, lower surface*.—Smooth, glabrous; matte.

*Color*.—Developing leaves and leaflets, upper surface: Close to N137B. Developing leaves and leaflets, lower surface: Close to 137C. Fully expanded leaves and leaflets, upper surface: Close to N137A; venation, close to 144B. Fully expanded leaves and leaflets, lower surface: Close to 147B; venation, close to 143D.

*Petioles*.—Length: About 6 cm. Diameter: About 4 mm. Strength: Moderately strong. Texture and luster, upper and lower surfaces: Smooth, glabrous; semi-glossy. Color, upper surface: Close to N137A. Color, lower surface: Close to 143D.

Inflorescence description:

*Appearance and arrangement*.—Double inflorescence form with ray florets forming acropetally on a receptacle; inflorescences positioned above the foliar plane on strong peduncles; inflorescences face mostly upright; freely flowering habit with about eight to twelve open inflorescences per plant at one time.

*Fragrance*.—None detected.

*Time to flower*.—Plants flower continuously from spring until late summer in The Netherlands; early flowering habit, plants begin flowering about ten to twelve weeks after sticking unrooted cuttings.

*Post-production longevity*.—Inflorescences maintain good substance for about two to three weeks on the plant; inflorescences persistent.

*Inflorescence buds*.—Height: About 1.1 cm. Diameter: About 1.8 cm. Shape: Globular. Texture and luster: Smooth; glossy. Color: Close to 144B.

*Inflorescence size*.—Diameter: About 8.8 cm. Depth (height): About 4.5 cm. Disc diameter: About 1.1 cm. Receptacle height: About 4 mm. Receptacle diameter: About 1.2 cm. Receptacle color: Close to 144B.

*Ray florets*.—Quantity per inflorescence: About 80 to 90 arranged in about six to eight whorls. Length: About 5 cm to 6 cm. Width: About 3 cm. Shape: Lanceolate. Apex: Obtuse. Base: Cuneate. Margin: Entire. Aspect: Initially upright to roughly perpendicular to the peduncle; somewhat concave. Texture and luster, upper and lower surfaces: Smooth, glabrous; matte. Color: When opening, upper and lower surfaces: Center, close to 158B and towards the margins and base, close to 70B. Fully opened, upper and lower surfaces: Center, close to 158C and towards the margins and base, close to 70B; venation similar to lamina color; colors do not change with subsequent development.

*Disc florets*.—Quantity per inflorescence: About 50 to 60; disc florets are inconspicuous. Length: About 1.3 cm. Diameter: About 3 mm. Shape: Tubular, elongated; apices obtuse. Texture and luster: Smooth, glabrous; matte. Color, when opening and fully opened, inner and outer surfaces: Close to 1B.

*Phyllaries*.—Quantity per inflorescence: About six arranged in a single whorl. Length: About 2.5 cm. Width: About 1 cm. Shape: Lanceolate. Apex: Acute. Base: Cuneate. Margin: Entire. Texture and luster, upper and lower surfaces: Smooth, glabrous; matte. Color, upper and lower surfaces: Close to 137A; venation, close to 137A.

*Peduncles*.—Length, terminal peduncle: About 6.5 cm. Diameter, terminal peduncle: About 4 mm. Aspect: Mostly erect to slightly outwardly. Strength: Moderately strong. Texture and luster: Smooth, glabrous; semi-glossy. Color: Close to 144B.

*Reproductive organs*.—Androecium: Present on disc florets only. Stamen quantity per floret: One. Filament length: About 1.1 cm. Filament color: Close to 12B. Anther size: About 4 mm by 5 mm. Anther color: Close to 17B. Pollen amount: Moderate. Pollen color: Close to 17B. Gynoecium: Present on disc florets only. Pistil quantity per floret: One. Pistil length: About 1.3 cm. Style length: About 1.1 cm. Style color: Close to 144D. Stigma diameter: Less than 1 mm. Stigma shape: Round. Stigma color: Close to 144C. Ovary color: Close to N144C. Seeds: To date, seed development has not been observed on plants of the new *Dahlia*.

Pathogen & pest resistance: To date, plants of the new *Dahlia* have not been observed to be resistant to pathogens and pests common to *Dahlia* plants.

Temperature tolerance & garden performance: Plants of the new *Dahlia* tolerate high temperatures about 35° C. and short periods of low temperatures about 5° to 10° C. Plants of the new *Dahlia* have been observed to have good garden performance.

It is claimed:

1. A new and distinct *Dahlia* plant named 'Dodahyproswi' as illustrated and described.

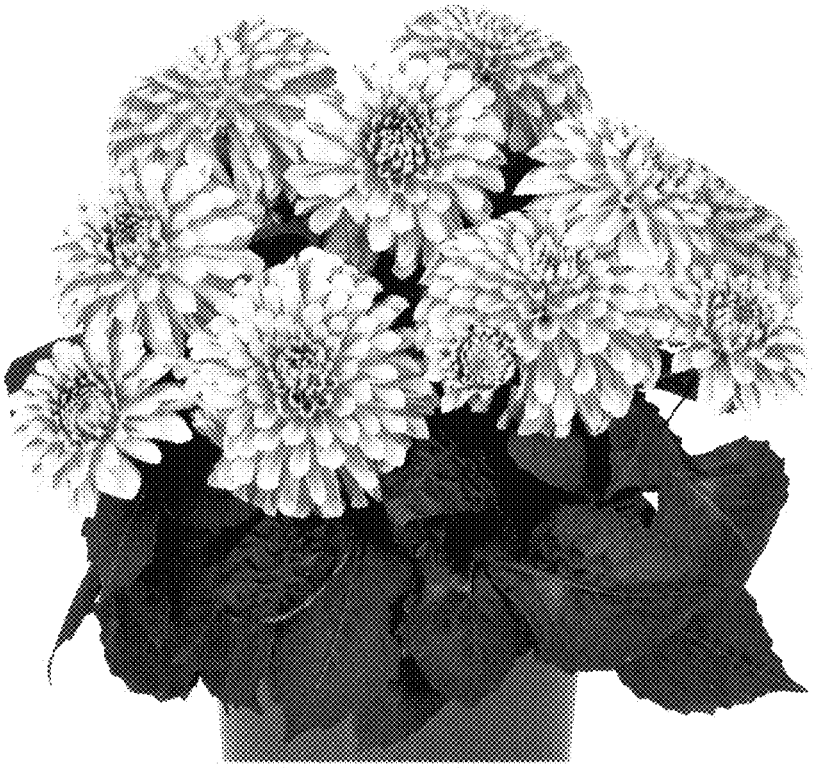

* * * * *